United States Patent [19]

Ife et al.

[11] Patent Number: 5,006,535
[45] Date of Patent: Apr. 9, 1991

[54] SUBSTITUTED HETEROCYLIC 4-AMINOQUINOLINE DERIVATIVES AS GASTRIC ACID SECRETION INHIBITORS

[75] Inventors: Robert J. Ife, Stevenage; Thomas H. Brown, Tewin; Colin A. Leach, Stevenage, all of England

[73] Assignee: Smith Kline & French Laboratories Ltd., Welwyn Garden City, United Kingdom

[21] Appl. No.: 315,368

[22] Filed: Feb. 23, 1989

[30] Foreign Application Priority Data

Feb. 25, 1988 [GB] United Kingdom ............... 8804447

[51] Int. Cl.$^5$ ................... C07D 215/44; A61K 31/44
[52] U.S. Cl. .................................. 514/313; 546/159
[58] Field of Search ..................... 546/159; 514/313

[56] References Cited

U.S. PATENT DOCUMENTS

| 2,652,398 | 9/1953 | Kaye ............................... 546/163 |
| 3,470,186 | 9/1969 | Hanifin et al. .................... 546/160 |
| 3,755,332 | 8/1973 | Wasley et al. ..................... 546/160 |
| 4,806,549 | 2/1989 | Ife et al. ........................... 546/159 |
| 4,806,550 | 2/1989 | Ife et al. ........................... 546/159 |

FOREIGN PATENT DOCUMENTS

| 0259174 | 3/1988 | European Pat. Off. . |
| 2106612 | 5/1972 | France . |
| 2047244 | 11/1980 | United Kingdom . |

OTHER PUBLICATIONS

Hanifin et al., J. Med. Chem. 12(5):1096–1097(1969); 4-anilino-3-quinolinecarboxylic acids and esters.
Morrison and Boyd; Organic Chemistry, Boston; Allan and Bacon, 1979, pp. 1004–1006.
Hanifin et al., "Synth. Anilino-3-Quinolinecarboxylic Acids & Esters", J. Med. Chem. vol. 12 (9) pp. 1096–1097 (1969).

Primary Examiner—Mukund J. Shah
Assistant Examiner—E. C. Ward
Attorney, Agent, or Firm—Dara L. Dinner; Janice E. Williams; Edward T. Lentz

[57] ABSTRACT

Substituted 4-aminoquinazoline derivatives which are inhibitors of gastric acid secretion. A compound of the invention is ethyl 8-methoxy-4-(4-methyl-3-thienylamino)quinoline-3-carboxylate.

13 Claims, No Drawings

SUBSTITUTED HETEROCYLIC 4-AMINOQUINOLINE DERIVATIVES AS GASTRIC ACID SECRETION INHIBITORS

The present invention relates to novel substituted quinoline derivatives, processes for their preparation, intermediates useful in their preparation, pharmaceutical compositions containing them and their use in therapy.

Substituted quinoline derivatives having activity as inhibitors of gastric acid secretion are known in the art. In particular, U.S. Pat. No. 4,343,804 and EP 259174-A disclose series of compounds in which the 4-position of the quinoline ring is substituted by a phenylamino ring which itself may be optionally substituted. The present invention relates to quinoline compounds which are substituted by alternative novel substituents in the 4-position of the quinoline ring and which have also been found to be potent inhibitors of gastric acid secretion.

Accordingly, the present invention provides, in a first aspect, a compound of structure (I):

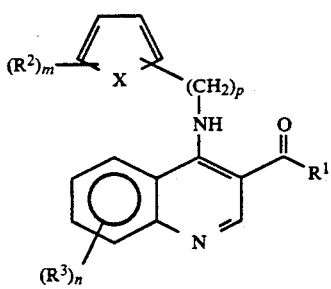

in which
R$^1$ is hydrogen, C$_{1-6}$alkyl, C$_{1-6}$alkoxy, C$_{1-6}$alkoxyC$_{1-6}$alkyl, C$_{3-6}$cycloalkyl, C$_{3-6}$cycloalkylC$_{1-6}$alkyl, phenyl or phenylC$_{1-6}$alkyl, the phenyl groups being optionally substituted;
R$^2$ is hydrogen, C$_{1-6}$alkyl, C$_{1-6}$alkoxy, CO$_2$H or CO$_2$C$_{1-6}$alkyl;
m is 1, 2 or 3;
p is 0 to 4;
R$^3$ is hydrogen, C$_{1-6}$alkyl, phenyl, C$_{1-6}$alkoxy, C$_{1-6}$alkylthio, C$_{1-6}$alkanoyl, amino, C$_{1-6}$alkylamino, di-C$_{1-6}$alkylamino, halogen, trifluoromethyl or cyano;
n is 1 or 2; and
X is S, O, NH or NC$_{1-4}$alkyl;
or a salt thereof.

Suitably, R$^1$ is hydrogen, C$_{1-6}$alkyl, C$_{1-6}$alkoxy, C$_{1-6}$alkoxyC$_{1-6}$alkyl, C$_{3-6}$cycloalkyl, C$_{3-6}$cycloalkylC$_{1-6}$alkyl, phenyl or phenylC$_{1-6}$alkyl, the phenyl groups being optionally substituted. Preferably R$^1$ is hydrogen, C$_{1-6}$alkyl, C$_{1-6}$alkoxy or C$_{1-6}$alkoxyC$_{1-6}$alkyl. Most preferably R$^1$ is C$_{1-6}$alkyl or C$_{1-6}$alkoxy, in particular C$_{1-6}$alkyl, such as ethyl, n-propyl or i-propyl.

Suitably R$^2$ is hydrogen, C$_{1-6}$alkyl, C$_{1-6}$alkoxy, CO$_2$H or CO$_2$C$_{1-6}$alkyl. Preferably R$^2$ is hydrogen or C$_{1-6}$alkyl.

Suitably m is 1 to 3; preferably m is 1 or 2.

Suitably p is 0 to 4; preferably p is 0 or 1; most preferably p is 0.

Suitably, n is 1 or 2 and at least one group R$^3$ is in the 8-position of the quinoline ring. Preferably n is 1 and the group R$^3$ is in the 8-position of the quinoline ring.

Suitably R$^3$ is hydrogen, C$_{1-6}$alkyl, phenyl, C$_{1-6}$alkoxy, C$_{1-6}$alkylthio, C$_{1-4}$alkanoyl, amino, C1-6alkylamino, diC$_{1-6}$-alkylamino, halogen, trifluoromethyl or cyano. Preferably R$^3$ is hydrogen, C$_{1-6}$alkyl or C$_{1-6}$alkoxy; most preferably, R$^3$ is C$_{1-6}$alkyl or C$_{1-6}$alkoxy, for example methyl or methoxy.

Suitably X is S, O, NH or NC$_{1-4}$alkyl; preferably X is sulphur.

C$_{1-6}$alkyl groups (either alone or as part of another group) can be straight or branched.

Phenyl C$_{1-6}$alkyl groups include for example benzyl phenylethyl, phenylpropyl and phenylbutyl groups. In addition also included are such groups in which the alkyl portion is branched e.g. 1-methylbenzyl.

Substituted phenyl and phenyl C$_{1-6}$alkyl groups R$^1$ include, for example phenyl groups substituted by 1 to 3 substituents as hereinbefore described for substituted phenyl groups R$^2$.

It will be appreciated that compounds of structure (I) in which one or more of R$^1$ to R$^3$ is a C$_{3-6}$alkyl group (either alone or as part of another group for example a benzyl or phenethyl group) may contain an asymmetric centre due to the presence of the C$_{3-6}$alkyl group. Such compounds will exist as two (or more) optical isomers (enantiomers). Both the pure enantiomers, racemic mixtures (50% of each enantiomer) and unequal mixtures of the two are included within the scope of the present invention. Further, all diastereomeric forms possible (pure enantiomers and mixtures thereof) are within the scope of the invention.

Compounds of structure (I) can form salts with acids and bases, and in particular form pharmaceutically acceptable acid addition salts with suitable organic and inorganic acids the nature of which will be apparent to persons skilled in the art. For example, pharmaceutically acceptable salts can be formed by reaction with hydrochloric, sulphuric, or phosphoric acids; aliphatic, aromatic or heterocyclic sulphonic acids or carboxylic acids such as for example, citric, maleic or fumaric acids.

In a further aspect, the present invention provides a process for the preparation of a compound of structure (I) which comprises (a) reaction of a compound of structure (II) with a compound of structure (III):

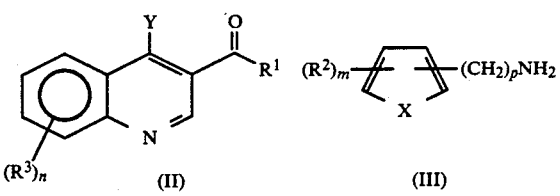

in which R$^1$, R$^2$, R$^3$, n, m, p, and X are as described for structure (I) and Y is a group displaceable by an amine;

(b) for compounds in which p is 1 to 4, reaction of a compound of structure (IV) with a compound of structure (V):

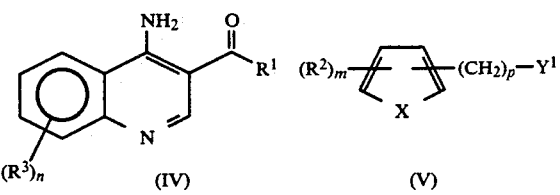

in which $R^1$, $R^2$, $R^3$, n, m and X are as described for structure (I) and $Y^1$ is a group displaceable by an amine;

(c) reduction of a compound of structure (VI):

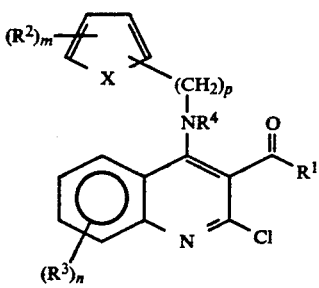

(VI)

in which $R^1$, $R^2$, $R^3$, n, m, p and X are as described for structure (I); and $R^4$ is hydrogen or a nitrogen protecting group;

(d) for compounds of structure (I) in which $R^1$ is other than $C_{1-6}$alkoxy, oxidation of a compound of structure (VII)

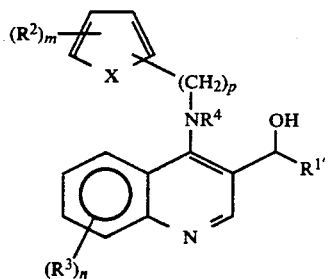

(VII)

in which $R^2$, $R^3$, p and n are as described for structure (I), $R^{1'}$ is a group $R^1$ other than $C_{1-6}$alkoxy and $R^4$ is hydrogen or a nitrogen protecting group; and thereafter if desired, removing any protecting groups;
converting a group $R^1$ into another group $R^1$;
converting a group $R^2$ into another group $R^2$;
forming a pharmaceutically acceptable salt.

Suitable groups Y displaceable by an amine, include for example, halo moieties, aryl or alkylsulphonates, for example, toluene-p-sulphonate or methane sulphonate, alkylthio, alkylsulphonyl, alkylsulphinyl, alkoxy or aryloxy. Preferably X is a halo moiety, for example, chloro or bromo, or aryloxy such as phenoxy.

Suitable leaving groups $Y^1$ will be apparent to those skilled in the art and include for example a halo moiety, preferably chloro or bromo.

Suitable nitrogen protecting groups $R^4$ will be apparent to those skilled in the art for example as described in "Protective Groups in Organic Synthesis" T. W. Greene, 1981 (Wiley).

The reaction between compounds of structure (II) and compounds of structure (III) is carried out in an organic solvent at a temperature of between ambient and reflux temperature of the solvent used. Suitable solvents include, for example, tetrahydrofuran, dioxan or anisole. Preferably the reaction is carried out at reflux temperature in dioxan as a solvent.

The reaction between compounds of structure (IV) and compounds of structure (V) is carried out in an inert organic solvent at a temperature of between ambient and reflux temperature of the solvent used, preferably in the presence of a strong base. Suitable solvents include for example, dimethylsulphoxide or tetrahydrofuran. Suitable bases include, for example, lithium diisopropylamide or dimsyl sodium.

The reduction of a compound of structure (VI) is carried out by for example hydrogenation, over a noble metal catalyst in a suitable solvent. Suitably the reaction is carried out over a palladium on carbon catalyst in ethanol as a solvent, or using a zinc catalyst in acetic acid.

The compounds of structure (VI) can be prepared from the corresponding compounds of structure (VIII)

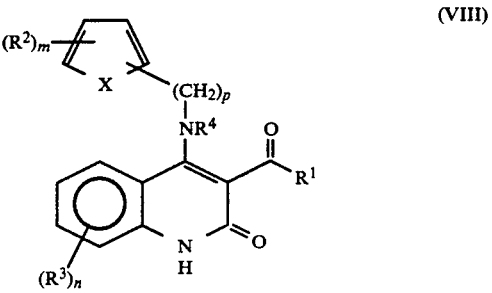

(VIII)

in which $R^1$, $R^2$, $R^3$, $R^4$, n, m, p and X are as hereinbefore described, by reaction with, for example, phosphorus oxychloride.

The oxidation of a compound of structure (VII) is carried out in a suitable solvent in the presence of an oxidising agent. Suitable oxidising agents include, for example, manganese dioxide or chromium trioxide.

Suitable interconversions of groups $R^1$ will be apparent to those skilled in the art, for example compounds of structure (I) in which $R^1$ is $C_{2-6}$alkyl, $C_{3-6}$cycloalkyl$C_{2-6}$alkyl or optionally substituted phenyl$C_{1-6}$-alkyl can be prepared by alkylation of the following compounds of structure (IA) :

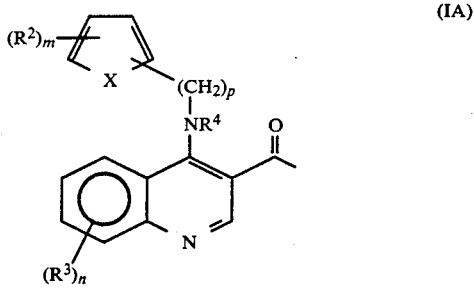

(IA)

in which $R^2$, $R^3$, m, n and p are as described for structure (I) and $R^4$ is hydrogen or a nitrogen protecting group.

The alkylation of compounds of structure (IA) is carried out in the presence of an alkylating agent in a suitable organic solvent at a temperature of between ambient and reflux temperature of the solvent used in the presence of a strong base. Suitable alkylating agents include, for example alkyl or aralkyl halides such as methyl or benzyl iodide and dialkyl sulphates such as dimethyl or diethylsulphate. Suitable strong bases include, for example, sodium hydride, lithium diisopropylamide or dimsyl sodium (the sodium salt of dimethyl sulphoxide). Subsequent removal of any protecting groups present affords the desired compounds of structure (I).

The intermediates of structure (II), (IV), (VI), (VII) and (VIII) can be prepared by standard techniques.

The intermediates of structure (III) and (V) are commercially available or can be prepared by standard techniques.

The compounds of structure (I) and their pharmaceutically acceptable salts exert an anti-secretory effect by inhibition of the gastrointestinal H+K+ATPase enzyme (Fellenius, E., Berglindh, T., Sachs, G., Olke, L., Elander, B., Sjostrand, S. E., and Wallmark, B., 1981, Nature, 290, 159–61).

In a further aspect therefore the present invention provides compounds of structure (I) and pharmaceutically acceptable salts thereof for use in therapy. The compounds of structure (I) and their pharmaceutically acceptable salts inhibit exogenously and endogenously stimulated gastric acid secretion and are useful in the treatment of gastrointestinal diseases in mammals, in particular humans. Such diseases include, for example, gastric and duodenal ulcers, aspiration pneumonitis and Zollinger-Ellison Syndrome.

Further, the compounds of structure (I) can be used in the treatment of other disorders where an anti-secretory effect is desirable for example in patients with gastritis, NSAID induced gastritis, acute upper intestinal bleeding, in patients with a history of chronic and excessive alcohol consumption, and in patients with gastro oesophageal reflux disease (GERD).

In therapeutic use, the compounds of the present invention are usually administered in a standard pharmaceutical composition. The present invention therefore provides in a further aspect pharmaceutical compositions comprising a compound of structure (I) or a pharmaceutically acceptable salt thereof and a pharmaceutically acceptable carrier.

The compounds of structure (I) and their pharmaceutically acceptable salts which are active when given orally can be formulated as liquids, for example syrups, suspensions or emulsions, tablets, capsules and lozenges.

A liquid formulation will generally consist of a suspension or solution of the compound or pharmaceutically acceptable salt in a suitable liquid carrier(s), for example, ethanol, glycerine, non-aqueous solvent, for example, polyethylene glycol, oils, or water with a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

A typical suppository formulation comprises a compound of formula (I) or a pharmaceutically acceptable salt thereof which is active when administered in this way, with a binding and/or lubricating agent such as polymeric glycols, gelatins or cocoa butter or other low melting vegetable or synthetic waxes or fats.

Preferably the composition is in unit dose form such as a tablet or capsule.

Each dosage unit for oral administration contains preferably from 1 to 250 mg (and for parenteral administration contains preferably from 0.1 to 25 mg) of a compound of the formula (I) or a pharmaceutically acceptable salt thereof calculated as the free base.

The present invention also provides a method of inhibiting gastric acid secretion which comprises administering to a mammal in need thereof an effective amount of a compound of the formula (I) or a pharmaceutically acceptable salt thereof; and a method of treatment of diseases of the stomach or intestine based on increased acid secretion which comprises administering to a mammal in need thereof an effective amount of a compound of the formula (I) or a pharmaceutically acceptable salt thereof.

The pharmaceutically acceptable compounds of the invention will normally be administered to a subject for the treatment of gastro-intestinal diseases and other conditions caused or exacerbated by gastric acidity. The daily dosage regimen for an adult patient may be, for example, an oral dose of between 1 mg and 500 mg, preferably between 1 mg and 250 mg, or an intravenous, subcutaneous, or intramuscular dose of between 0.1 mg and 100 mg, preferably between 0.1 mg and 25 mg, of the compound of the formula (I) or a pharmaceutically acceptable salt thereof calculated as the free base, the compound being administered 1 to 4 times per day. Suitably the compounds will be administered for a period of continuous therapy, for example for a week or more.

In addition, the compounds of the present invention can be co-administered with further active ingredients, such as antacids (for example magnesium carbonate or hydroxide and aluminium hydroxide), non-steroidal anti-flammatory drugs (for example indomethacin, aspirin or naproxen), steroids, or nitrite scavengers (for example ascorbic acid or aminosulphonic acid), or other drugs used for treating gastric ulcers (for example pirenzipine, prostanoids for example 16,16 dimethyl PGE$_2$, or histamine H$_2$-antagonists (for example, cimetidine).

The following Examples illustrate the invention. Temperatures are recorded in degrees centigrade.

EXAMPLE 1

Ethyl 8-methoxy-4-(4-methyl-3-thienylamino)quinoline 3-carboxylate

The sodium salt of 3-amino-4-methylthiophene-2-carboxylic acid (7.2 g, 0.04 mol) and ethyl 8-methoxy-4-chloroquinoline-3-carboxylate (5.39 g, 0.02 mol) in toluene (75 ml), ethanol (55 ml) and glacial acetic acid (10 ml) were stirred at room temperature for five days. The solvents were removed by evaporation at reduced pressure to give a dark-green slurry. 10% aqueous sodium carbonate was added and the insoluble solid filtered off, washed well with water and dried. This material was crystallised from ethyl acetate (with charcoaling) to give the title compound as pale yellow crystals (2.15 g), m.p. 162°–164°.

C₁₈H₁₈N₂O₃S

Found C, 63.19; H, 5.32; N, 8.20; S, 9.23%
Requires C, 63.14; H, 5.30; N, 8.18; S, 9.36%

EXAMPLE 2

3-Butyryl-4-(2-ethyl-3-thienylamino)-8-methoxyquinoline (a) Methyl 4-amino-5-ethylthiophene-2-carboxylate hydrochloride (5 g, 0.023 mol) and sodium hydroxide solution (2N, 25 ml) were heated under reflux for one hour. Evaporation under reduced pressure gave a solid sodium salt of —COOH, of which (2.2 g, 0.0113 mol) was suspended in toluene (50 ml) containing a solution of 3-butyryl-4-chloro-8-methoxyquinoline (1.5 g, 0.0057 mol) in ethanol (20 ml). Glacial acetic acid (1 ml) was added and the reaction mixture was stirred at room temperature for five days. The solvents were removed under reduced pressure and the residue basified with dilute sodium carbonate solution. The resulting solid was collected by filtration and dried, 1.85 g, m.p. 228°–232°.

(b) 5-Ethyl-4-(4-(8-methoxyquinolyl)amino)thiophene-3-carboxylic acid (1.44 g, 0.00362 mol) and copper-bronze (0.3 g) in quinoline (30 ml) was heated under reflux for fifteen minutes. Chloroform (300 ml) was added to the cooled mixture and the copper filtered off over Hiflo. The chloroform was extracted with 2N.HCl (5×150 ml). The chloroform extracts were then washed with aqueous sodium bicarbonate and water, dried and evaporated to dryness to give a brown-yellow oil which solidified on standing. This material was crystallised twice from acetone to give the title compound as yellow crystals (0.42 g), m.p. 119°–121°.

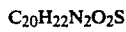
C₂₀H₂₂N₂O₂S

Found C, 67.38; H, 6.25; N, 7.89; S, 9.08%
Requires C, 67.77; H, 6.26; N, 7.40; S, 9.05%

EXAMPLE 3

3-Butyryl-4-(2-methoxycarbonyl-3-thienylamino-8-methoxyquinoline

3-Butyryl-4-chloro-8-methoxyquinoline (0.5 g, 0.0019 mol) and methyl 3-aminothiophene-2-carboxylate (0.6 g, 0.0038 mol) were heated in an oil bath at 140° for one hour. After cooling the residual solid was dissolved in chloroform and the chloroform solution extracted with 1N.HCl (3×50 ml). The chloroform solution was then washed with aqueous sodium carbonate solution (×2) and water, dried and evaporated to give a yellow solid residue. This was crystallised (with charcoaling) from absolute ethanol to give the title compound as a yellow solid (0.55 g), m.p. 159°–161°.

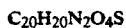
C₂₀H₂₀N₂O₄S

Found C, 62.22; H, 5.10; N, 7.24; S, 8.42%
Requires C, 62.48; H, 5.24; N, 7.29; S, 8.34%

EXAMPLE 4

3-Butyryl-4-(3-methyl-2-thienylamino)-8-methoxyquinoline

3-Butyryl-4-chloro-8-methoxyquinoline (3.6 g, 0.0137 mol) and 2-amino-3-methylthiophene (3.4 g, 0.03 mol) in 1,4 dioxan (30 ml) under a nitrogen atmosphere were stirred at room temperature for 20 hours. The solvent was evaporated under reduced pressure to give an oil. The oil was taken up in dichloromethane and extracted with 2N hydrochloric acid (3×100 ml). The dichloromethane extracts were then washed with sodium carbonate solution (100 ml), dried over magnesium sulphate, filtered and evaporated under reduced pressure to give a solid. The solid was purified by flash chromatography using a gradient elution of dichloromethane/methanol (0–5%, 500 ml). The fractions containing the product were combined and evaporated under reduced pressure to give a solid, (1.94 g), m.p. 130°–132°. Recrystallization from ethyl acetate gave the title compound, (1.7 g), m.p. 132°–133°.

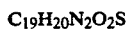
C₁₉H₂₀N₂O₂S

Found C 66.89, H 5.93, N 8.25, S 9.35%
Requires C 67.03, H 5.92, N 8.23, S 9.42%

EXAMPLE 5

Ethyl 8-methoxy-4-(4-methoxy-3-thienylamino)quinoline-3-carboxylate

Ethyl 8-methoxy-4-chloroquinoline-3-carboxylate (1.5 g, 0.0056 mol) and 4-methoxy-3-aminothiophene (1.46 g, 0.0112 mol) in 1,4 dioxan (20 ml) were heated under reflux for 4 hours. The solid which had formed was collected by filtration and dried. The solid was dissolved in chloroform, washed with sodium carbonate solution (50 ml), then water, dried over magnesium sulphate, filtered and evaporated under reduced pressure to give a yellow solid. Recrystallization from ethyl acetate gave the title compound, (1.53 g) m.p. 176°–178°.

C₁₈H₁₈N₂O₄S

Found C 60.47, H 5.18, N 7.84, S 8.71%
Requires C 60.32, H 5.06, N 7.82, S 8.95%

EXAMPLE A

A tablet for oral administration is prepared by combining

|  | Mg/Tablet |
|---|---|
| Compound of structure (I) | 100 |
| lactose | 153 |
| Starch | 33 |
| crospovidone | 12 |
| microcrystalline cellulose | 30 |
| magnesium stearate | 2 |
|  | 330 mg | into a 9 mm tablet.

EXAMPLE B

An injection for parenteral administration is prepared from the following

|  | % w:w |
|---|---|
| Compound of structure (I) | 0,50% (w:v) |
| 1 M citric acid | 30% (v:v) |
| sodium hydroxide (qs) | to pH 3.2 |

| | % w:w |
|---|---|
| water for injection EP | to 100 ml |

The compound of Structure (I) is dissolved in the citric acid and the pH slowly adjusted to pH 3.2 with the sodium hydroxide solution. The solution is then made up to 100 ml with water, sterilised by filtration and sealed into appropriately sized ampoules and vials.

Biological Data

A. H+K+ATPase Activity

The effects of a single high concentration (100 μM) of a compound of structure (I) on K-stimulated ATPase activity in lyophilised gastric vesicles was determined. Preferred compounds of structure (I) were also tested over a range of concentrations to determine IC$_{50}$ values.

(i) Preparation of lyophilised gastric vesicles (H/K-ATPase)

Lyophilised gastric vesicles were prepared from pig fundic mucosa after the method of Keeling et. al. (Biochem. Pharmacol., 34, 2967, 1985).

(ii) K+-stimulated ATPase activity

K+-stimulated ATPase activity was determined at 37° in the presence of the following: 10 mM Pipes/Tris buffer pH 7.0, 2 mM MgSO$_4$, 1 mM KCl, 2 mM Na$_2$ATP and 3-6 μg protein/ml lyophilised gastric vesicles. After incubation for 30 minutes, the inorganic phosphate hydrolysed from ATP was determined by the method of Yoda and Hokin (Biochem. Biophys. Res. Commun. 40, 880, 1970).

Compounds of structure (I) were dissolved in dimethylsulphoxide which up to the highest concentration used had no effect on K+-stimulated ATPase activity.

The effect of the highest concentration of each compound of structure (I) on the recovery of a standard amount of inorganic phosphate was also determined.

The results obtained are shown in the following table:

| Example No. | ATPase IC$_{50}$ (μM) |
|---|---|
| 1 | 0.53 |
| 2 | 1.4 |
| 3 | 21% @ 100 μM |
| 4 | 2.3 |
| 5 | 3.4 |

B. Rat Lumen Perfused Stomach (pentagastrin stimulated gastric acid secretion).

Using a modification of the procedure described by Ghosh & Schild (Br. J. Pharmacology, 13, 54, 1958), the compounds of the following examples were found on i.v. administration at a concentration of 10 μmole/kg to cause an inhibition of pentagastrin stimulated gastric acid secretion as indicated in the following table. Results are given as % inhibition at 10 μmole/kg or ED$_{50}$ (μM/kg):

| Example No. | ED$_{50}$ (μM/Kg) % inhibition |
|---|---|
| 1 | 4.62 |
| 2 | 61% |
| 3 | 48% |
| 4 | 58% |
| 5 | 41% |

What is claimed is:

1. A compound of structure (I):

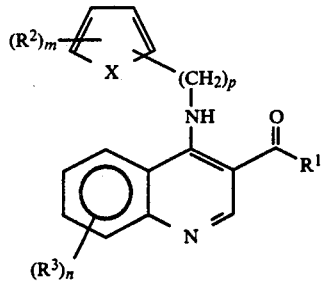

in which R$^1$ is hydrogen, C$_{1-6}$ alkyl, C$_{1-6}$ alkoxy, C$_{1-6}$alkoxyC$_{1-6}$alkyl, C$_{3-6}$ cycloalkyl, C$_{3-6}$cycloalkylC$_{1-6}$alkyl, phenyl, phenylC$_{1-6}$alkyl, the phenyl group being optionally substituted from 1 to 3 times by members independently selected from the group consisting of hydrogen, C$_{1-6}$ alkyl, C$_{1-6}$ alkoxy, amino, C$_{1-6}$ alkylthio, halogen, cyano, hydroxy, C$_{1-6}$ alkanoyl and trifluromethyl;

R$^2$ is hydrogen, C$_{1-6}$ alkyl, C$_{1-6}$ alkoxy, CO$_2$H or CO$_2$C$_{1-6}$ alkyl;

m is 1 to 3;

p is 0 to 4;

R$^3$ is hydrogen, C$_{1-6}$alkyl, phenyl, C$_{1-6}$alkoxy, C$_{1-6}$alkylthio, C$_{1-6}$ alkanoyl, amino, C$_{1-6}$alkylamino, di-C$_{1-6}$ alkylamino, halogen, trifluromethyl or cyano;

n is 1 or 2; and

X is S, or O, provided that when X is oxygen, n and p are both 1, and R$^1$ is H or ethoxy, then R$^3$ is other than 6-chloro;

or a pharmaceutically acceptable salt thereof.

2. A compound according to claim 1 in which the heterocyclic ring is bonded to the 4-amino quinoline substituent when p=0, or to the methylene chain when p=1-4 via the 3-position of said heterocyclic ring.

3. A compound according to claim 2 in which m is 1 and R$^2$ is hydrogen.

4. A compound according to claim 3 in which n is 1 and R$^3$ is a C$_{1-6}$alkyl or C$_{1-6}$alkoxy group.

5. A compound according to claim 4 in which the group R$^3$ is in the 8-position of the quinoline ring.

6. A compound according to claim 1 which is ethyl 8-methoxy-4-(4-methyl-3-thienylamino)quinoline-3-carboxylate.

7. A compound according to claim 1 which is 3-butyryl-4-(2-ethyl-3-thienylamino)-8-methoxyquinoline.

8. A compound according to claim 1 which is 3-butyryl-4-(2-methoxycarbonyl-3-thienylamino-8-methoxyquinoline.

9. A compound according to claim 1 which is 3-butyryl-4-(3-methyl-2-thienylamino)-8-methoxyquinoline.

10. A compound according to claim 1 which is ethyl 8-methoxy-4-(4-methoxy-3-thienylamino)quinoline-3-carboxylate.

11. A pharmaceutical composition comprising a compound according to of claim 1 or a pharmaceutically acceptable salt thereof and a pharmaceutically acceptable carrier.

12. A method of inhibiting gastric acid secretion which comprises administering to a mammal in need thereof an effective amount of a compound according to claim 1.

13. A method of treatment of gastrointestinal diseases and other conditions caused or exacerbated by gastric acidity which comprises administering to a mammal in need thereof an effective amount of a compound according to claim 1.

* * * * *